US00PP25612P3

(12) United States Plant Patent
Deng et al.

(10) Patent No.: US PP25,612 P3
(45) Date of Patent: Jun. 2, 2015

(54) *CALADIUM* PLANT NAMED 'UF 4412'

(50) Latin Name: *Caladium×hortulanum*
Varietal Denomination: UF 4412

(71) Applicants: Zhanao Deng, Riverview, FL (US); Brent K. Harbaugh, Bradenton, FL (US)

(72) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 229 days.

(21) Appl. No.: 13/815,693

(22) Filed: Mar. 14, 2013

(65) Prior Publication Data

US 2014/0283265 P1 Sep. 18, 2014

(51) Int. Cl.
*A01H 5/12* (2006.01)
*A01H 5/02* (2006.01)

(52) U.S. Cl.
CPC ..... *A01H 5/02* (2013.01)
USPC ..... Plt./373

(58) Field of Classification Search
USPC ..... Plt./373
See application file for complete search history.

*Primary Examiner* — Anne Grunberg
(74) *Attorney, Agent, or Firm* — Christopher & Weisberg, P.A.

(57) ABSTRACT

A new and distinct cultivar of *Caladium* plant named 'UF 4412', characterized by its mounding growth habit, heart-shaped leaves that have a large red center, red primary veins, netted greyed-purple secondary veins, and green margins, and plants that are attractive in containers or landscapes.

7 Drawing Sheets

ACKNOWLEDGMENT OF FEDERAL RESEARCH SUPPORT

This invention was made with government support under FLA-BRA-04162 awarded by the Cooperative State Research, Education, and Extension Service, USDA. The government has certain rights in the invention.

Genus and species: *Caladium×hortulanum.*
Cultivar denomination: 'UF 4412'.

CROSS-REFERENCE TO RELATED APPLICATION n/a

BACKGROUND OF THE NEW CULTIVAR

The present invention relates to a new and distinct cultivar of *Caladium* plant, botanically known as *Caladium×hortulanum*, commercially referred to as a strap leaf-type or lance leaf-type *Caladium* and hereinafter referred to by the name 'UF 4412'.

*Caladiums* (also referred to as *Caladium* plants) are ornamental aroids frequently used as pot and landscape plants for their colorful foliage and ease of growing. The objective of the Inventors' breeding program is to create new *Caladium* cultivars that have compact growth habit, numerous leaves, attractive foliage, and exceptional container and landscape performance.

*Caladium* cultivar 'UF 4412' originated from a cross between 'Florida Sweetheart' (U.S. Plant Pat. No. 8,526) and 'Red Flash' (commercial cultivar, not patented) that was made in Bradenton, Fla., in spring 2004. The new *Caladium* cultivar 'UF 4412' was discovered and selected by the inventors as a single plant in Wimauma, Fla., in winter 2005. The

*Caladium* cultivar 'UF 4412' has been found to retain its distinctive characteristics through at least seven generations of successive asexual propagations conducted in Wimauma, Fla., via tuber divisions since April of 2006.

Plant Breeder's Rights for this cultivar have not been applied for. 'UF 4412' has not been made publicly available more than one year prior to the filing of this application.

SUMMARY OF THE INVENTION

The new *Caladium* cultivar has not been observed under all possible environmental conditions. The phenotype may vary somewhat with variations in environment such as temperature, light intensity, water status, fertilizer rate and type, without, however, any variance in genotype.

The following are the most outstanding and distinguishing characteristics of this new *Caladium* cultivar when grown under (normal or standard) horticultural practices in Wimauma, Fla. The combination of these characteristics distinguishes 'UF 4412' as a new and distinct cultivar of *Caladium:*

1. Symmetrical, outwardly arching and rounded plant form;
2. Mounding, dense and bushy growth habit;
3. Heart-shaped lance-type leaves that have a large red center, red primary veins, netted greyed-purple secondary veins throughout the leaf, and dark green margins; and
4. Attractive plants in containers or sunny or shady landscapes.

The new *Caladium* cultivar 'UF 4412' differs from its female parent, 'Florida Sweetheart' (U.S. Plant Pat. No. 8,526), in the following characteristics:

1. Plants of 'UF 4412' are taller than plants of 'Florida Sweetheart';

2. Leaves of 'UF 4412' are longer and wider than the leaves of 'Florida Sweetheart'; and
3. Leaves of 'UF 4412' have a large red center and netted greyed-purple secondary veins, whereas leaves of 'Florida Sweetheart' have a light rose center and dark rose veins.

The new *Caladium* cultivar 'UF 4412' differs from its male parent, 'Red Flash', in the following characteristics:

1. Plants of 'UF 4412' are shorter than plants of 'Red Flash';
2. Leaves of 'UF 4412' are of a lance type, whereas leaves of 'Red Flash' are of a fancy type;
3. Leaves 'UF 4412' are significantly smaller than leaves of 'Red Flash';
4. Petioles of 'UF 4412' attach to the base of leaves, whereas petioles of 'Red Flash' attach to the lower back of the leaves; and
5. Leaves of 'UF 4412' are non-spotted, whereas leaves of 'Red Flash' are spotted.

The new *Caladium* cultivar 'UF 4412' can also be compared to the *Caladium* cultivar 'Florida Red Ruffles', disclosed in U.S. Plant Pat. No. 13,136. In side-by-side comparisons conducted in Wimauma, Fla., plants of the new *Caladium* cultivar differed from plants of 'Florida Red Ruffles' in the following characteristics:

1. Plants of 'UF 4412' were taller and wider than plants of 'Florida Red Ruffles';
2. Leaves of 'UF 4412' were longer and wider than leaves of 'Florida Red Ruffles';
3. Leaves of 'UF 4412' were heart-shaped and had netted veins, whereas leaves of 'Florida Red Ruffles' were lanceolate and lacked netted veins; and
4. Leaves of 'UF 4412' had a red center, whereas leaves of 'Florida Red Ruffles' had a dark red center.

The new *Caladium* cultivar 'UF 4412' can also be compared to the *Caladium* cultivar 'UF 44-4', disclosed in U.S. Plant Pat. No. 24,680. In side-by-side comparisons conducted in Wimauma, Fla., plants of the new *Caladium* cultivar 'UF 4412' differed from plants of 'UF 44-4' in the following characteristics:

1. Plants of 'UF 4412' were taller and wider than plants of 'UF 44-4';
2. Leaves of 'UF 4412' had a large red center, whereas leaves of 'UF 44-4' had a darker red center and wider green margins; and
3. Leaves of 'UF 4412' had obvious netted greyed-purple secondary veins.

The new *Caladium* cultivar 'UF 4412' can also be compared to the *Caladium* cultivar 'UF 4424,' disclosed in co-pending U.S. application Ser. No. 13/815,705. In side-by-side comparisons conducted in Wimauma, Fla., plants of 'UF 4412' differed from plants of 'UF 4424' in the following characteristics:

1. Leaves of 'UF 4412' were heart-shaped while leaves of 'UF 4424' were lanceolate with an elongated acute apex;
2. Margins of the leaves of 'UF 4412' were less undulate than margins of the leaves of 'UF 4424';
3. Leaves of 'UF 4412' had netted greyed-purple secondary veins, whereas leaves of 'UF 4424' lacked noticeable netted veins; and
4. Leaves of 'UF 4412' were not waxy while leaves of 'UF 4424' were waxy.

DESCRIPTION OF THE FIGURES

The accompanying photographs (as shown in FIGS. 1-7) illustrate the overall appearance of the new *Caladium* cultivar. These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION OF THE CULTIVAR

Figure 1:
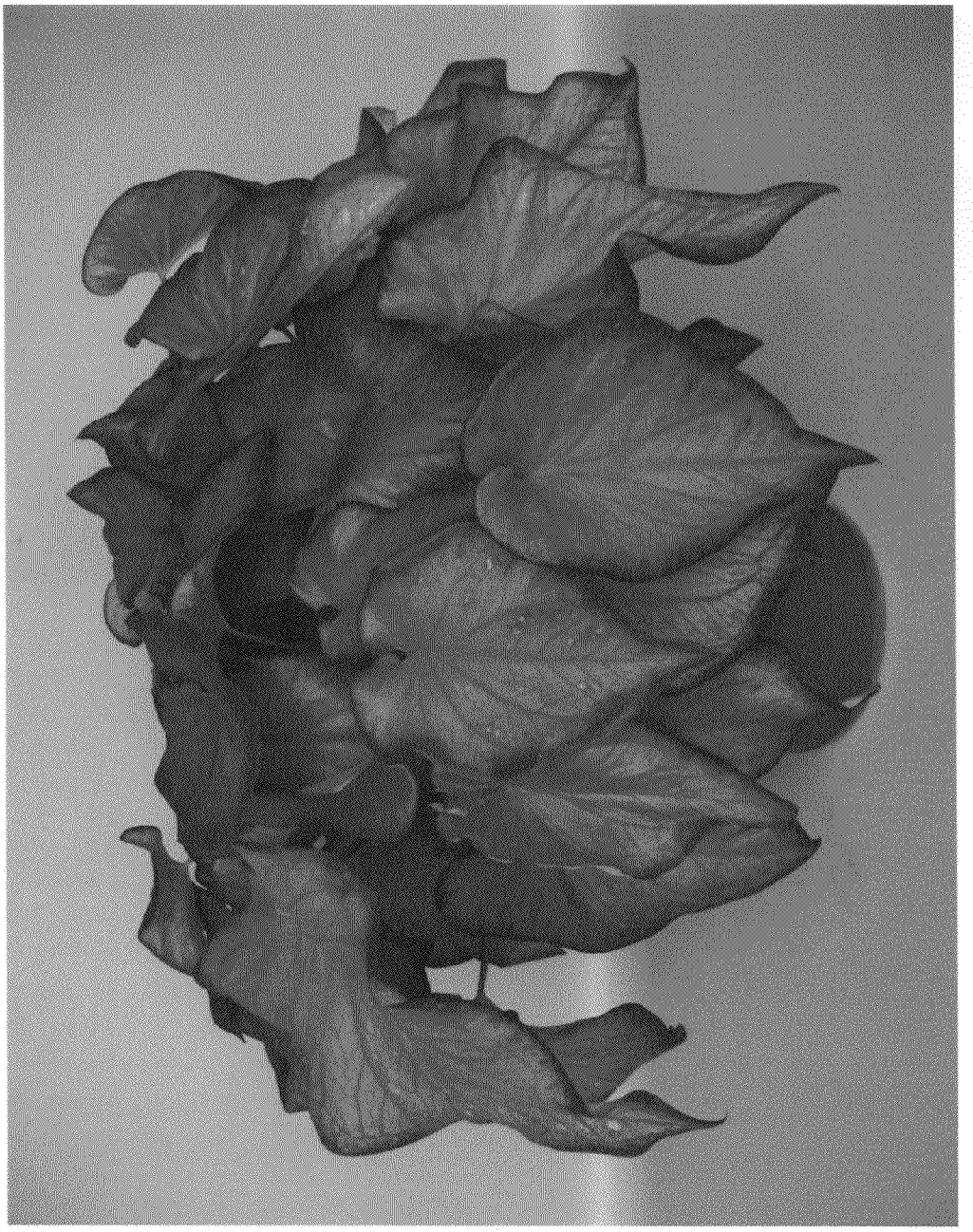
FIG. 1 shows a photograph of a side view of a typical plant of the new *Caladium* cultivar 'UF 4412' grown in a 20-cm diameter container in a shadehouse.
Figure 2:
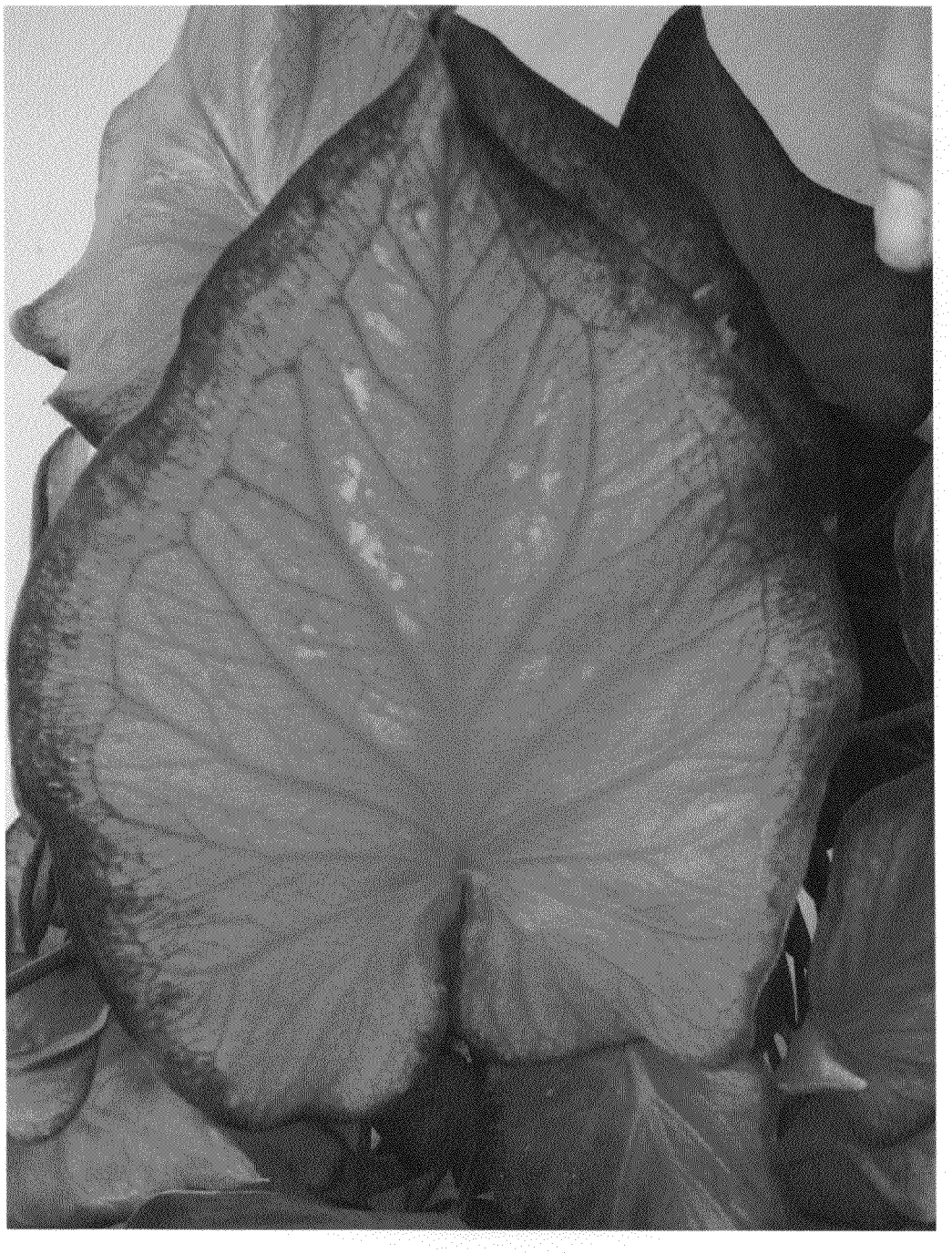
FIG. 2 shows a photograph of a top view of a typical leaf of the new *Caladium* cultivar 'UF 4412' grown in a 20-cm diameter container in a shadehouse.
Figure 3:
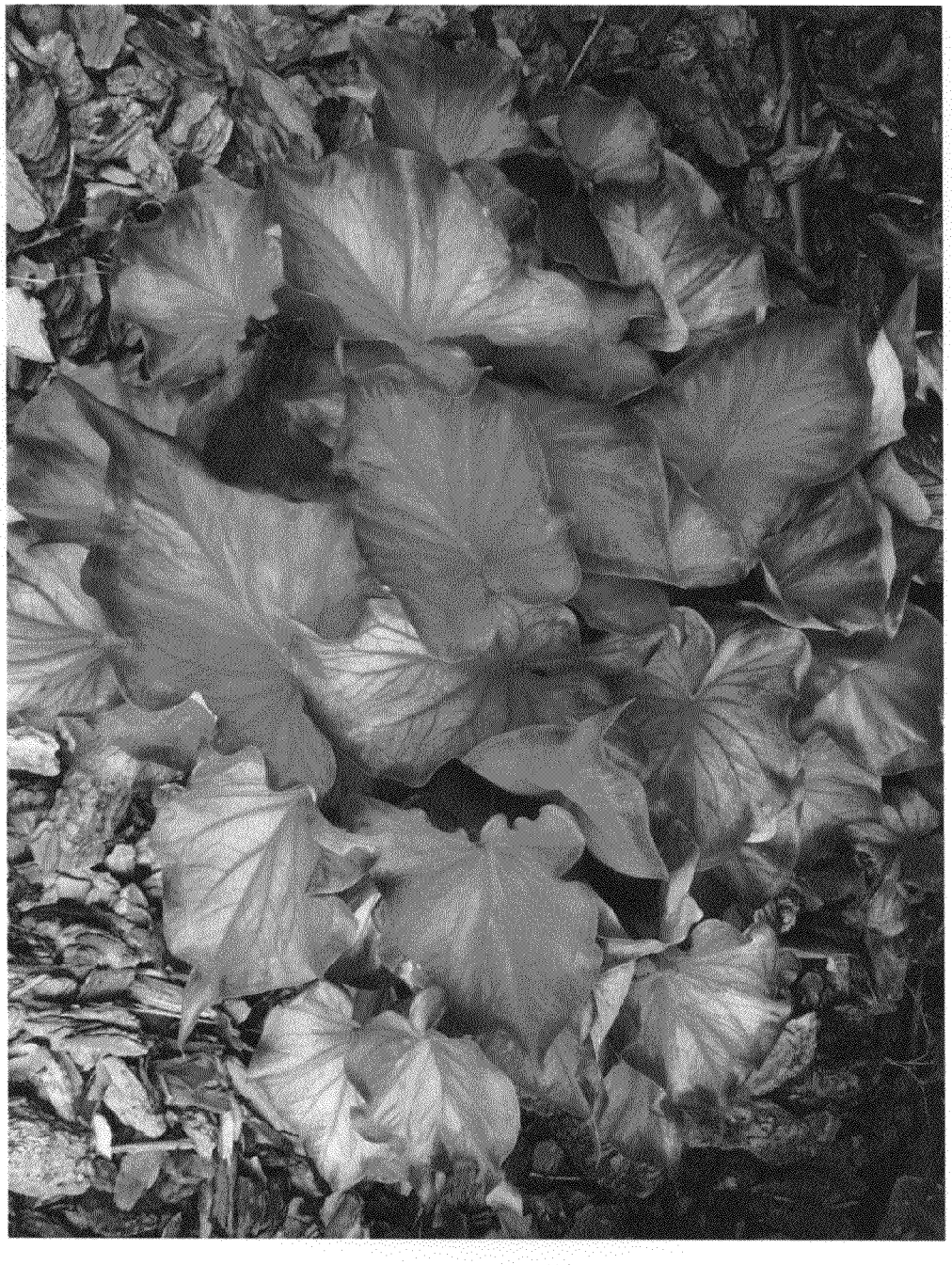
FIG. 3 shows a photograph of a top view of typical plants of the new *Caladium* cultivar 'UF 4412' grown in an outdoor nursery.
Figure 4:
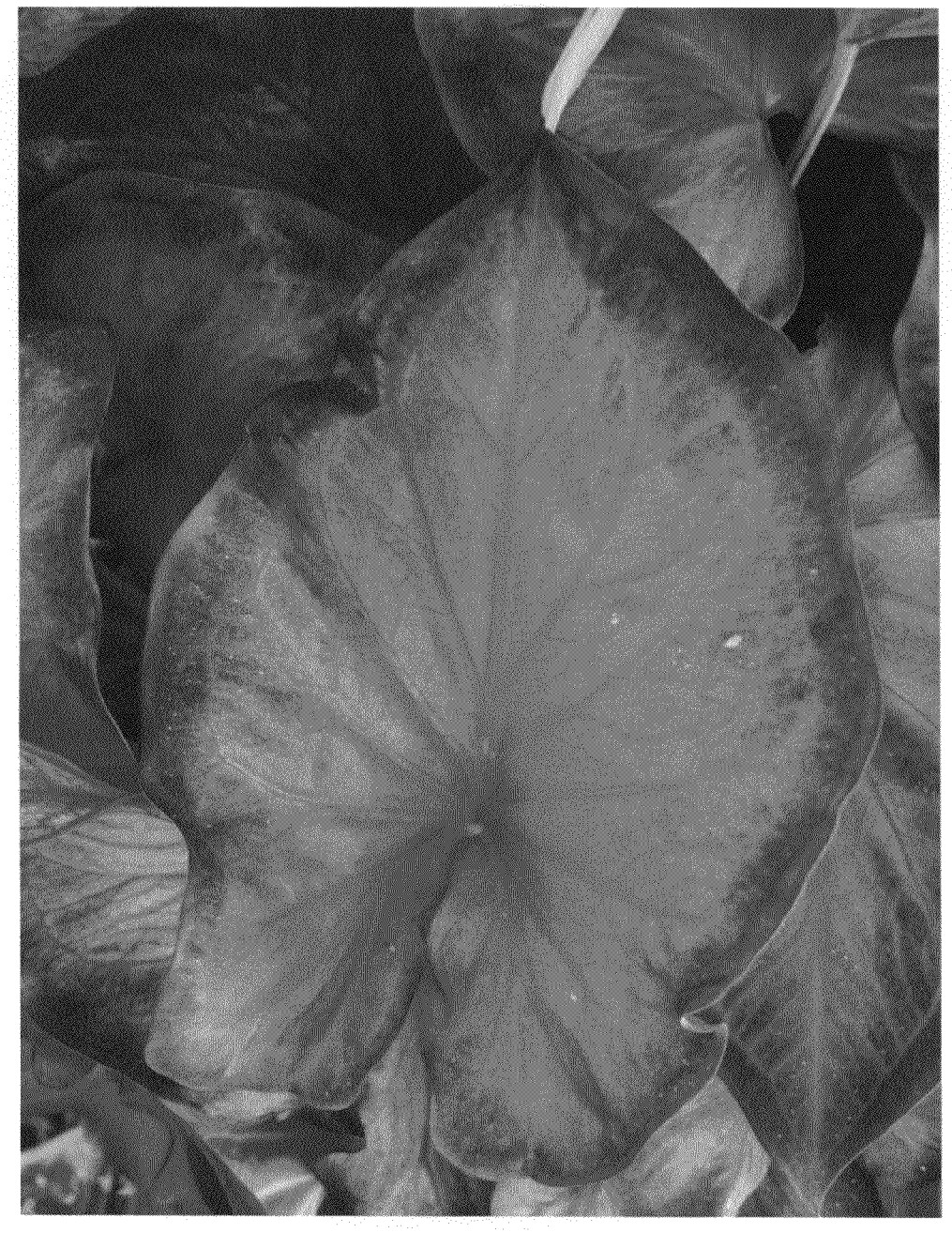
FIG. 4 shows a photograph of a top view of a typical leaf of the new *Caladium* cultivar 'UF 4412' grown in an outdoor nursery.
Figure 5:
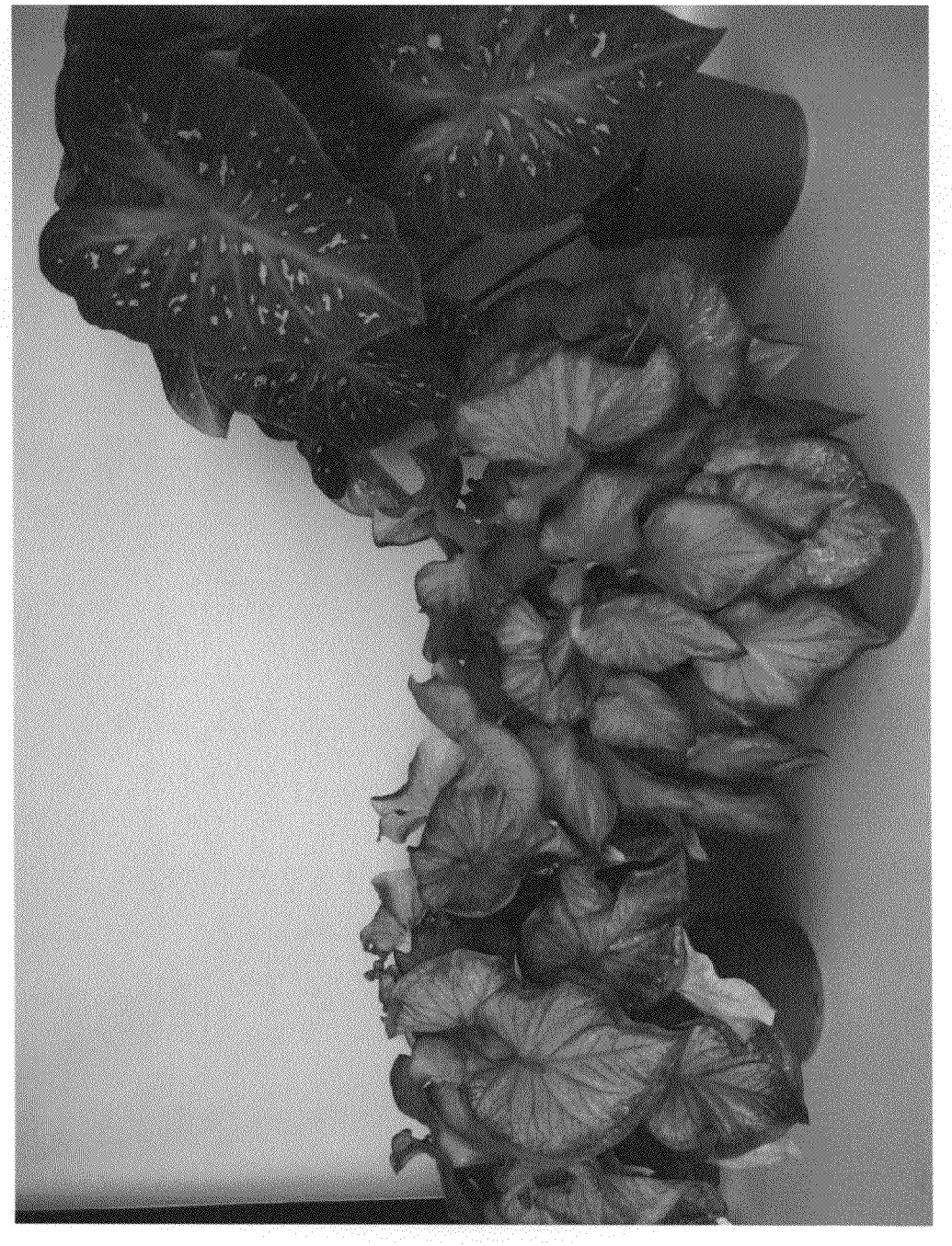
FIG. 5 shows a photograph of a side view of typical plants of 'Florida Sweetheart' (left), 'UF 4412' (center), and 'Red Flash' (right) grown in 20-cm diameter container in a shadehouse.
Figure 6:
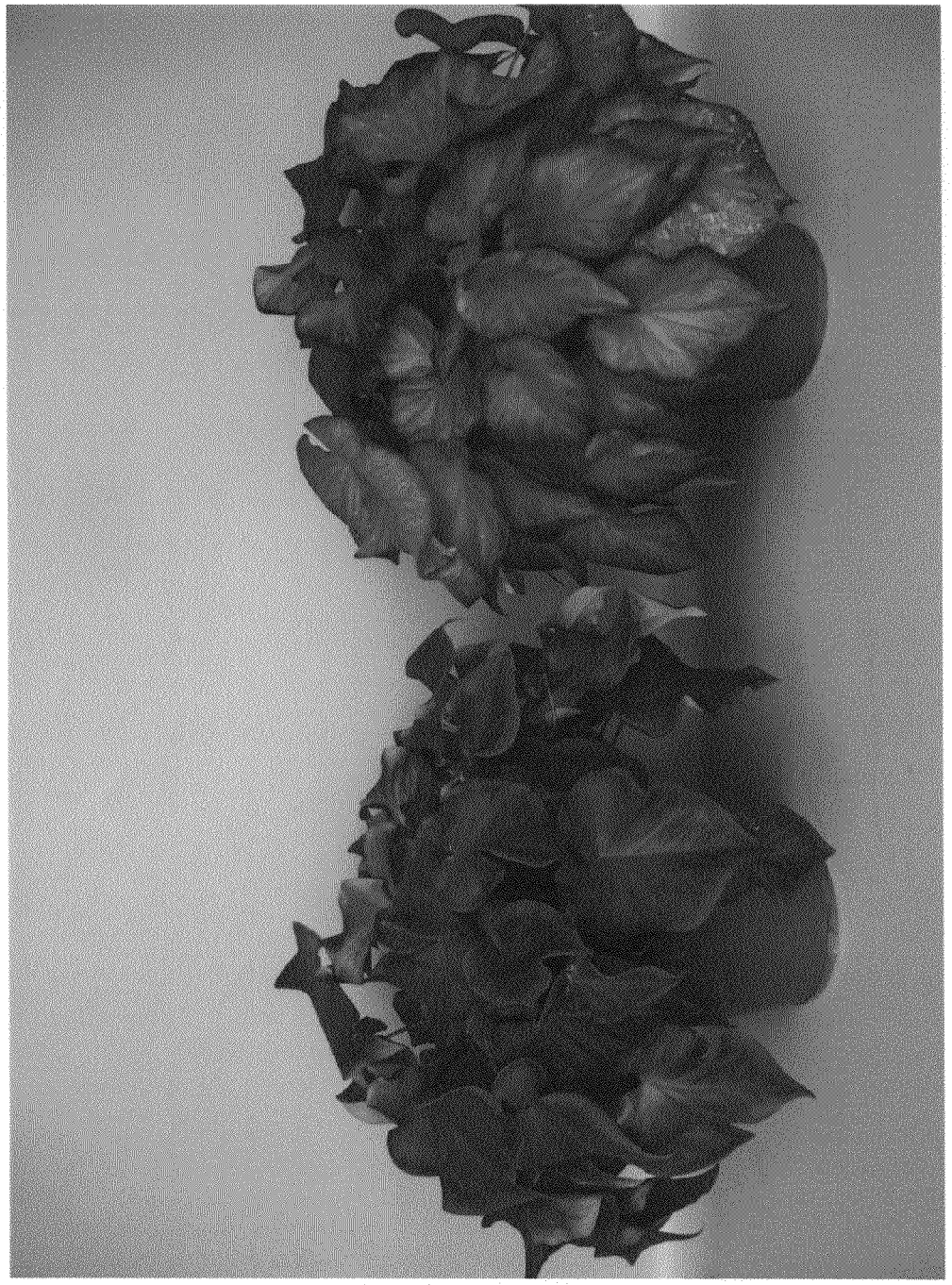
FIG. 6 shows a photograph of a side view of typical plants of 'Florida Red Ruffles' (left) and 'UF 4412' (right) grown in 20-cm diameter container in a shadehouse.
Figure 7:
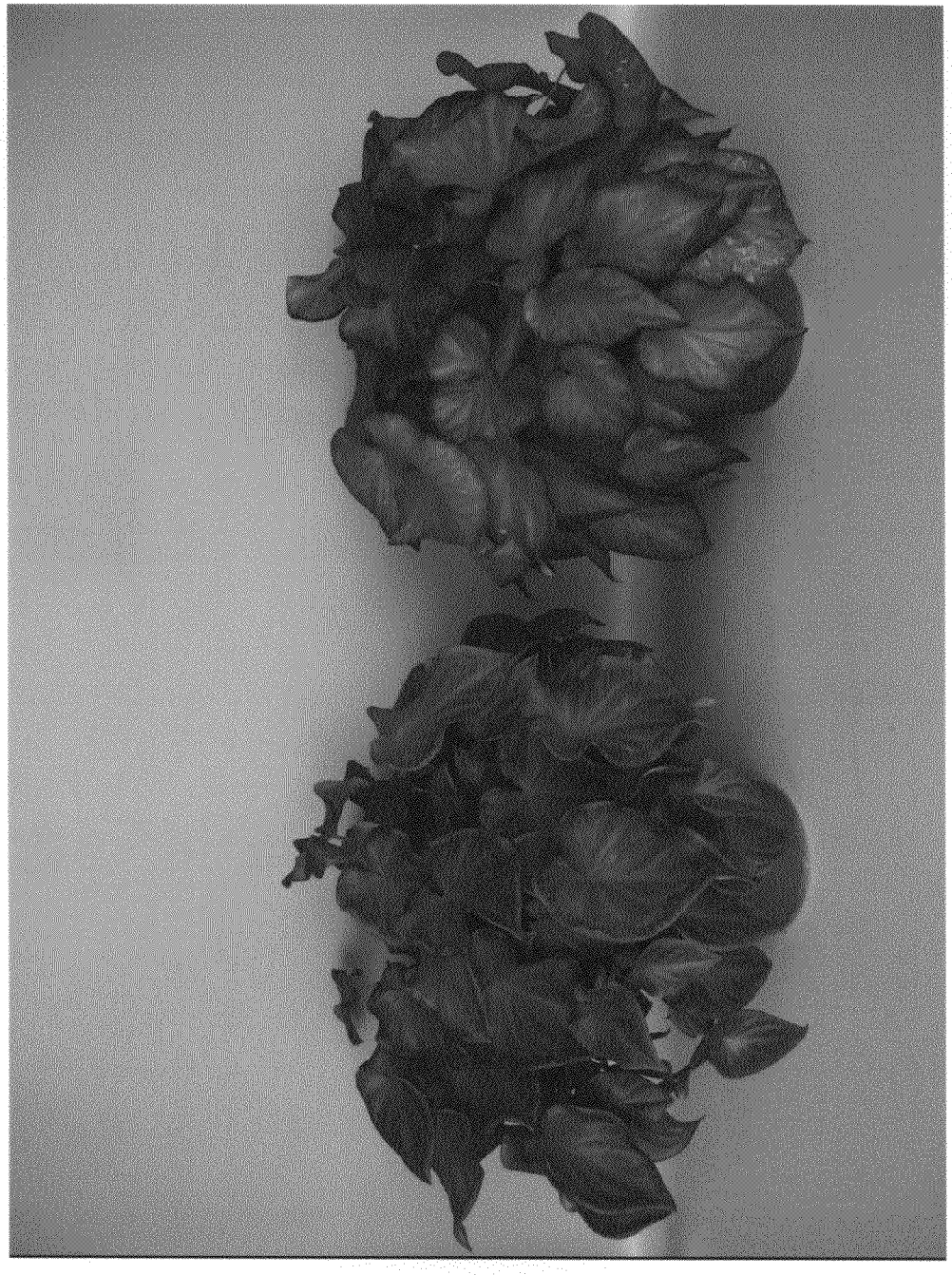
FIG. 7 shows a photograph of a side view of typical plants of 'UF 44-4' (left) and 'UF 4412' (right) grown in 20-cm diameter container in a shadehouse.

In the following description, color references are made to The Royal Horticultural Society Colour Chart, 1986 Edition, except where general terms of ordinary dictionary significance are used. The features of 'UF 4412' described herein are shown in FIGS. 1-7.

DESCRIPTION OF GROWING CONDITIONS

The following observations and measurements describe plants grown in 20-cm containers in Wimauma, Fla., during the summer in a polypropylene-covered shadehouse and plants grown in ground beds in Wimauma, Fla., during the late summer in an outdoor nursery. All plants were grown under conditions and practices similar to those generally used in commercial *Caladium* production.

During the production of the plants, day temperatures ranged from approximately 23.5° C. to 34.4° C., night temperatures ranged from approximately 20.5° C. to 23.5° C., and light levels were approximately 944 foot-candles in the shadehouse and 9744 foot-candles in the outdoor nursery. Plants grown in the shadehouse were approximately seven weeks from planting tubers when the photographs and the detailed description were taken. Plants grown in the outdoor nursery were approximately three months from planting tuber pieces when the photographs and the detailed description were taken.

BOTANICAL DESCRIPTION

Botanical classification:

*Family*.—Araceae.

*Botanical name*.—*Caladium×hortulanum*.

*Common name*.—*Caladium*.

*Cultivar*.—'UF 4412' (*Caladium×hortulanum* cultivar UF 4412).

Parentage:

*Female or seed parent*.—'Florida Sweetheart' (U.S. Plant Pat. No. 8,526).

*Male or pollen parent*.—'Red Flash', not patented.

Propagation:

*Type*.—By tubers and by tuber divisions.

*Time to initiate roots, summer*.—Approximately seven to ten days at 32° C.

*Time to initiate roots, winter*.—Approximately two to three weeks at 24° C.

Tuber description: Jumbo-sized (6.4 to 8.9 cm in diameter) tubers are multi-segmented, bearing six to eight dominant buds.

*Height of tubers*.—2 to 5 cm.

*Diameter of tubers*.—Up to 9 cm.

*Texture*.—Thick, starchy; slightly brittle.

*Color*.—Epidermis, Close to brown (RHS 200B); Interior, yellow-orange (RHS 15A).

*Root description*.—Dense, thick and white fleshy roots.

Plant description:

*Type*.—Herbaceous perennial.

*Plant form*.—Upright, outwardly arching and symmetrical plant.

*Growth habit*.—Compact and mounding, dense foliage, suitable for 10.0 cm to 25.0-cm containers. Leaf petioles arising from tubers; petioles mostly semi-upright and curving outwardly with development.

*Plant height, from soil level to top of leaf plane, shadehouse-grown plants*.—Approximately 40 cm.

*Plant height, from soil level to top of inflorescences, shadehouse-grown plants*.—Approximately 42 cm.

*Plant spread, shadehouse-grown plants*.—Approximately 72 cm×69 cm.

*Plant height, from soil level to top of leaf plane, outdoor nursery-grown plants*.—Approximately 31 cm.

*Plant height, from soil level to top of inflorescences, outdoor nursery-grown plants*.—Approximately 33 cm.

*Plant spread, outdoor nursery-grown plants*.—Approximately 58 cm×50 cm.

Foliage description (shadehouse-grown and outdoor-grown):

*Length, shadehouse-grown plants*.—Approximately 20.5 cm.

*Width, shadehouse-grown plants (flattened)*.—Approximately 14.5 cm.

*Length, outdoor nursery-grown plants*.—Approximately 20 cm.

*Width, outdoor nursery-grown plants (flattened)*.—Approximately 12 cm.

*Shape*.—Ovate.

*Apex*.—Acuminate to acute.

*Base*.—Cordate.

*Margin*.—Entire; slightly undulate.

*Texture, upper surface*.—Smooth, glabrous.

*Texture, lower surface*.—Smooth, glabrous; glaucous.

*Venation pattern*.—Pinnate.

Leaf color, shadehouse-grown plants:

*Developing and fully expanded leaves*.—Upper surface: Center: Close to red (RHS 53C and 53D) with small blotches of red (RHS 36C) and green (RHS 139A) and specs of white (RHS 155A). Border and margins: Close to green (RHS 139A). Basal notch: Close to red (RHS 53C). Venation: Midrib: Close to red (RHS 46A) Primary and netted veins: Close to greyed-purple (RHS 185A and RHS 184A). Lower surface: Center: Close to greyed-purple (RHS 185C) with blotching of grey-green (RHS 191B) and mottling of greyed-yellow (RHS 162D). Border and margins: Close to greyed-green (RHS 191A). Venation: Midrib: Close to greyed-red (RHS 182D, but lighter). Primary veins: Close to greyed-green (RHS 197A and 197B).

Leaf color, outdoor nursery-grown plants:

*Developing leaves*.—Upper surface: Center: Close to red (RHS 53C) and blotches of green (RHS 139A) and specs of white (RHS 155C). Border and margins: Close to green (RHS 139A). Venation: Midrib and primary veins: Red (RHS 53A). Lower surface: Center: Close to greyed-purple (RHS 185C) with blotches of greyed-green (RHS 191B). Border and margins: Close to greyed-green (RHS 191A). Venation: Midrib and primary veins: Close to greyed-red (RHS 182D, but lighter).

*Fully expanded leaves*.—Upper Surface: Center: Close to red-purple (RHS 60C) and blotches of green (RHS 139A) and specs of white (RHS 155C). Border and margins: Close to yellow-green (RHS 147A). Venation: Midrib and primary veins: Close to red (RHS 53A). Lower surface: Center: Close to red-purple (RHS 60B) with blotches of greyed-green (RHS 191 B) near margins. Border and margins: Close to greyed-green (RHS 191A). Venation: Midrib and primary vein: Close to greyed-red (RHS 182D, but lighter).

Petiole:

*Aspect*.—Mostly erect, curving outwardly with development.

*Length, shadehouse-grown plants*.—Approximately 26.0 to 35.0 cm.

*Diameter, distal, shadehouse-grown plants*.—Approximately 3.4 mm.

*Diameter, proximal, shadehouse-grown plants*.—Approximately 6.6 mm.

*Length, outdoor nursery-grown plants*.—Approximately 22.0 cm to 26.0 cm.

*Diameter, distal, outdoor nursery-grown plants*.—Approximately 3.4 mm.

*Diameter, proximal, outdoor nursery-grown plants*.—Approximately 5.5 mm.

*Strength*.—Strong; flexible.

*Color, shadehouse-grown plants*.—Close to greyed-red (RHS 182D) with small blotches of brown (RHS 200B) or long streaks of black (RHS 202A).

*Color, proximal, outdoor nursery-grown plants*.—Close to greyed-red (RHS 182D, but lighter) with long streaks of brown (RHS 200A).

*Wing length, shadehouse-grown plants*.—Approximately 4.0 cm to 6.0 cm.

*Wing diameter, shadehouse-grown plants*.—Approximately 4.2 mm to 5.5 mm.

*Wing length, outdoor nursery-grown plants*.—Approximately 3.5 cm to 5.0 cm.

*Wing diameter, outdoor nursery-grown plants*.—Approximately 4.9 mm to 5.7 mm.

*Wing color, shadehouse-grown plants*.—Close to greyed-red (RHS 182D, but lighter) with small blotches and streaks of brown (RHS 200B).

*Wing color, outdoor nursery-grown plants*.—Close to grey-green (RHS 196D) with dashes of greyed-green (RHS 197A).

Inflorescence description:

*Inflorescence arrangement*.—Upright hooded spathes surrounding a columnar spadix borne on an upright scape. Spadix carries sessile, simple female and male flowers separated into two zones. Female flowers arranged on the lower one-third of the spadix; male flowers arranged on the upper two-thirds of the spadix. Sterile flowers develop between female and male flower zones. Spadix constricts near the sterile flower zone.

*Fragrance*.—None detected.

*Natural flowering season/longevity*.—Plants of 'UF 44112' typically flower during spring or early summer in central Florida. Flowers develop about seven weeks after growth commence. Inflorescences last about four days before fading.

*Spathe*.—Length: Approximately 13.5 cm. Width: Distal: Approximately 3.0 cm. Proximal: Approximately 2.3 cm. Shape: Ovate to somewhat obovate. Apex: Acute to acuminate. Base: Tapering. Margin: Entire. Texture: Upper and lower surfaces: Smooth, glabrous. Color: Front surface: Upper two-thirds: Close to white (RHS 155A and 155B). Lower one-third: Close to yellow-green (RHS 147D) with streaks of yellow-green (RHS 147C). Rear surface: Upper two-thirds: Close to yellow-white (RHS 158C). Lower one-third: Close to yellow-green (RHS 147D) with streaks of yellow-green (RHS 147C).

*Spadix*.—Length, entire spadix: Approximately 6.5 cm. Length, male flower zone: Approximately 3.8 cm. Length, sterile flower zone: Approximately 1.3 cm. Length, female flower zone: Approximately 1.6 cm. Diameter, male flower zone: Approximately 7.6 mm. Diameter, sterile flower zone: Approximately 5.3 mm. Diameter, female flower zone: Approximately 8.3 mm. Shape: Spindle-shaped to columnar. Apex: Obtuse. Base: Obtuse. Aspect: Upright. Color, mature, male zone: Close to yellow-white (RHS 158A). Color, mature, sterile zone: Close to yellow (RHS 155B). Color, mature, female zone: Close to yellow (RHS 11C). Male flowers: Quantity per spadix: Approximately 78. Shape: Obovate. Height: Approximately 2 mm. Diameter: Approximately 3.7 mm. Anther color: Close to yellow (RHS 10B). Amount of pollen: Abundant. Female flowers: Quantity per spadix: Approximately 103. Shape: Obovate. Height: Approximately 2 mm. Diameter: Approximately 1 mm. Stigma color: Close to yellow (RHS 11B). Ovary color: Close to white (RHS 155D).

*Scape*.—Length: Approximately 24.5 cm. Diameter: Approximately 4.6 mm. Strength: Sturdy, flexible. Aspect: Erect. Texture: Smooth, glabrous, glaucous. Color, proximal: Close to greyed-red (RHS 182B) with streaks of greyed-purple (RHS 183C) or yellow-green (RHS 147C) with streaks of brown (RHS 200C) and greyed-purple (RHS 183C) Just below spathe: Close to yellow-green (RHS 148C or RHS 147D).

*Seed and fruit*.—Seed and fruit development has not been observed on inflorescences that were not hand-pollinated.

Disease/pest resistance: Plants of 'UF 4412' have been observed to be somewhat resistant to *Xanthomonas* leaf spot.

Temperature tolerance: Tolerant to temperatures ranging from approximately 7° C. to approximately 40° C.

Sunburn tolerance: Moderate to high level of tolerance to sunburns.

COMPARISON WITH KNOWN CULTIVARS

The new *Caladium* cultivar 'UF 4412' was evaluated for tuber production at the Gulf Coast Research and Education Center in Wimauma, Fla., in 2007, 2009, and 2010. The soil was EauGallie fine sand with about 1% organic matter and pH values between 6.2 and 7.4. *Caladium* plants were grown in the field using a plastic-mulched raised-bed system. In 2007, ground beds (81 cm wide, 20 cm high) were fumigated on 3 April with a mixture of 67% methyl bromide and 33% chloropicrin (by volume) at the rate of 196 $kg \cdot ha^{-1}$. *Caladium* seed pieces (tuber pieces, approximately 2.5×2.5×2.5 cm) were manually planted on 26 April with approximately 25.4 cm between-row spacing and approximately 15.2 cm in-row spacing. Drip tapes were buried under the plastic mulch and delivered approximately 6 mm of water to the bed per day. Fertigation (through the drip irrigation system) began when young *Caladium* plants emerged from the soil, supplying 6N-0.8P-3.9K soluble fertilizer at the rate of approximately 1.9 kg of $nitrogen \cdot ha^{-1} \cdot day^{-1}$ and a total 290 kg of $nitrogen \cdot ha^{-1}$ per growing season. Tubers (new crop) were dug from the soil, washed, and dried in early January 2008. Dried tubers from each experimental field plot were weighed, graded, and counted in late January 2008. Tuber grading was by the maximum diameter: Supper Mammoth (greater than 11.4 cm), Mammoth (8.9 to 11.4 cm), Jumbo (6.4 to 8.9 cm), No.1 (3.8 to 6.4 cm), and No. 2 (2.5 to 3.8 cm). Tuber grades and counts were converted into a Production Index (PI) to show the relative economic value of the harvested tubers per field plot: PI=8n (Supper Mammoth)+6n (Mammoth)+4n (Jumbo)+2n (No.1)+n (No.2), where n=number of tubers in the grade.

In 2009, field beds (81 cm wide, 20 cm high) were fumigated on 27 February with a mixture of 50% methyl bromide and 50% chloropicrin (by volume) at the rate of 196 $kg \cdot ha^{-1}$. *Caladium* seed pieces were planted 9 April at approximately 15-cm spacing between rows and in rows. The irrigation and fertigation system was the same as the one used in 2007, but one teaspoon (approximately seven grams) of the controlled-release fertilizer Osmocote® (15N-2.6P-10K, 5-6 months; Scotts Co., Marysville, Oh.) was applied to each plant on 21 July. Tubers were dug from the soil on 30 Nov. to 2 Dec. 2009, followed by washing, drying, weighing, grading, and counting as done in 2007.

In 2010, ground beds (91 cm wide, 20 cm high) were fumigated on 21 March with PIC-Clor®60 (39% 1,3-dichloropropene and 59.6% chloropicrin; Soil Chemicals Corp., Hollister, Calif.) at the rate of 426 $kg^{-1}$. *Caladium* seed pieces were planted on 9 April with 15-cm spacing between and in rows. A seepage irrigation system was used to maintain a water table below the *Caladium* root system. Approximately 14 grams of Osmocote® 15N-2.6P-10K (8-9 months) was applied to each plant on 18 May and again on 13 August. *Caladium* tubers were dug from the soil on 3-6 December. Tuber washing, drying, weighing, and grading were conducted as above described.

In each growing season, field plots were arranged in a randomized complete block fashion with three blocks, and each plot was 1.2 $m^2$ and was planted with 30 *Caladium* seed pieces. 'Florida Red Ruffles' and 'Florida Sweetheart' were included in each block. Analyses of variance were conducted using the PROC GLM procedure in SAS (SAS Institute, Cary, N.C.) to compare the tuber yield of 'UF 4412' to that of 'Florida Red Ruffles', 'Florida Sweetheart', and 'UF 4424'.

Table 1 shows the tuber weight, marketable tubers, production index, and grade distribution of 'UF 4412' grown in Wimauma, Fla. in 2007, 2009 and 2010. Values presented for each year are means of three plots in three randomized complete blocks.

As shown in Table 1, 'UF 4412' produced more marketable tubers than 'UF 4424' in 2009 but produced similar weights and similar number of marketable tubers in 2010.

As shown in Table 1, in tuber grade distribution, the majority (60% or more) of tubers 'UF 4412' produced were in the categories of No. 1, Jumbo, or Mammoth, which was similar to the size distribution of 'Florida Red Ruffles' and 'Florida Sweetheart'.

Table 2 shows a comparison of the plant height, number of leaves, leaf length, and leaf width of 'UF 4412' with 'Florida Sweetheart', 'Florida Red Ruffles', and 'UF 4424', approximately 4 months from planting 2.54-cm tuber propagules in ground beds in full sun in 2009 and 2010. Values presented are means of three years' data from three replications and three plants measured per plot per year.

TABLE 1

| | Tuber | | | Tuber distribution (%) | | | | |
|---|---|---|---|---|---|---|---|---|
| Cultivars | Weight (kg) | Production index | Marketable (no.) | Super mammoth | Mammoth | Jumbo | No. 1 | No. 2 |
| | | | | Year 2007 | | | | |
| 'UP 4412' | 3.5 | 148 a[z] | 75.0 a | | 3.3 | 13.7 | 44.4 | 38.6 |
| 'Florida Red Ruffles' | 2.7 | 85 b | 42.0 b | | 1.0 | 20.0 | 41.0 | 37.9 |
| 'Florida Sweetheart' | 3.3 | 105 b | 45.7 b | | 2.6 | 28.6 | 31.3 | 37.5 |
| LSD ($\alpha$ = 0.05) | NS | 41.76 | 18.46 | | NS | NS | NS | NS |
| | | | | Year 2009 | | | | |
| 'UP 4412' | 3.6 a | 146 a | 76.7 a | | 1.9 | 7.5 bc | 65.3 | 25.4 |
| 'Florida Red Ruffles' | 1.8 b | 72 b | 44.7 c | | | 4.4 c | 48.8 | 46.8 |
| 'Florida Sweetheart' | 3.9 a | 136 a | 67.3 ab | | 1.3 | 19.5 a | 38.9 | 40.3 |
| 'UP 4424' | 3.4 a | 135 a | 61.0 b | | 4.0 | 14.8 ab | 58.3 | 22.9 |
| LSD ($\alpha$ = 0.05) | 1.16 | 23.4 | 14.5 | | NS | 10.0 | NS | NS |
| | | | | Year 2010 | | | | |
| 'UF 4412' | 2.5 | 113 | 47.0 | | 4.7 | 19.2 | 56.1 a | 20.0 |
| 'Florida Red Ruffles' | 1.9 | 109 | 40.3 | | 2.4 | 41.1 | 36.7 ab | 19.9 |
| 'Florida Sweetheart' | 2.9 | 129 | 45.0 | | 9.2 | 42.4 | 20.8 b | 27.6 |
| 'UF 4424' | 2.4 | 108 | 44.3 | | 6.8 | 21.3 | 45.0 ab | 26.9 |
| LSD ($\alpha$ = 0.05) | NS | NS | NS | | NS | NS | 29.1 | NS |

[z]mean values with the same letter within columns are not significantly different at $P < 0.05$.
LSD: least significant difference; NS: not significantly different at $P < 0.05$.

As shown in Table 1, 'UF 4412' was more productive than 'Florida Sweetheart' in 2007 and was as productive as 'Florida Sweetheart' in 2009 and 2010. In the 2007 growing season, 'UF 4412' produced more marketable tubers (75.0 vs. 45.7) and had a greater PI (148 vs. 105) than 'Florida Sweetheart'. In the 2009 and the 2010 growing seasons, 'UF 4412' and 'Florida Sweetheart' produced similar amounts and similar marketable numbers of tubers and generated similar PIs: 3.6 kg of tubers vs. 3.9 kg in 2009 and 2.5 kg vs. 2.9 kg in 2010; 76.7 marketable tubers vs. 67.3 in 2009 and 47.0 vs. 45.0 in 2010; and a PI of 146 vs. 136 in 2009 and 113 vs. 129 in 2010.

As shown in Table 1, 'UF 4412' was more productive than 'Florida Red Ruffles' in two of the three growing seasons. 'UF 4412' produced more marketable tubers in 2007 (75.0 vs. 42.0) and in 2009 (76.7 vs. 44.7) and had a higher PI in 2007 (148 vs. 85) and in 2009 (146 vs. 72). In 2010, 'UF 4412' produced a greater amount and a larger number of tubers than 'Florida Red Ruffles', although the differences were not significant.

TABLE 2

| Cultivar | Plant height (cm) | Leaves (no.) | leaf length (cm) | Leaf width (cm) |
|---|---|---|---|---|
| 'UF 4412' | 35.7 a[z] | 25.6 | 25.1 a | 15.9 a |
| 'Florida Red Ruffles' | 17.9 c | 27.7 | 16.9 b | 10.0 c |
| 'Florida Sweetheart' | 22.9 c | 28.7 | 19.4 b | 13.4 b |
| 'UF 4424' | 28.6 b | 23.3 | 22.9 a | 13.2 b |
| LSD ($\alpha$ = 0.05) | 3.14 | NS | 2.69 | 1.17 |

[z]mean values with the same letter within columns are not significantly different at $P < 0.05$.
LSD = least significant difference; NS: not significantly different at $P < 0.05$.

As shown in Table 2, plants of 'UF 4412' had an average height of 35.7 cm after growing in full sun and sandy soil for about 4 months. Plants of 'UF 4412' were about 13 to 19 cm taller than plants of 'Florida Red Ruffles' or 'Florida Sweetheart'. Leaves of 'UF 4412' had an average size of 25.1 by 15.9 cm and were approximately 5 to 8 cm longer and approximately 2.5 to 6 cm wider than leaves of 'Florida Red Ruffles' and 'Florida Sweetheart'. Under these growing conditions, plants of 'UF 4412' were also taller than plants of 'UP 4424', and leaves of 'UF 4412' were wider than leaves of 'UF 4424'.

Table 3 shows landscape performance and sun burn tolerance of 'UF 4412' with 'Florida Sweetheart', 'Florida Red Ruffles', and 'UF 4424' when planted in ground beds in full sun in 2007, 2009 and 2010. Values presented are means of three replications in each year.

Landscape performance was evaluated on the same plots used for evaluating tuber production. A scale of 1 to 5 was used with 1 being very poor (few leaves and lack of vigor), and 5 being excellent (full plants, numerous leaves, and bright color display). Leaf sun burn tolerance also was evaluated on a scale of 1 to 5, with 1 being very susceptible to sun burns (leaves having numerous sun-damaged areas or holes) and 5 being resistant to sunburn (no visible sun-damaged areas). A total of eight evaluations were conducted- for plant performance and sunburn tolerance over three growing seasons in July, August, and September 2007, August, September, and October 2009, and September and October 2010.

TABLE 3

| | Performance rating | | | | | | | |
|---|---|---|---|---|---|---|---|---|
| | 2007 | | | 2009 | | | 2010 | |
| Cultivar | July | August | September | August | September | October | September | October |
| 'UF 4412' | 4.7 a[z] | 4.2 a | 4.3 a | 4.5 a | 4.8 a | 4.7 a | 4.7 a | 4.9 a |
| 'Florida Red Ruffles' | 3.8 b | 3.1 b | 2.9 b | 3.2 b | 3.7 b | 3.5 b | 2.9 c | 3.3 c |
| 'Florida Sweetheart' | 3.3 b | 3.1 b | 2.8 b | 4.7 a | 4.5 ab | 3.3 b | 4.7 a | 4.3 b |
| 'UF 4424' | —[y] | — | — | 4.7 a | 4.8 a | 4.5 a | 4.2 b | 4.2 b |
| LSD (α = 0.05) | 0.81 | 1.04 | 1.33 | 1.00 | 1.10 | 0.90 | 0.45 | 0.41 |
| | Sunburn tolerance rating | | | | | | | |
| | 2007 | | | 2009 | | | 2010 | |
| Cultivar | July | August | September | August | September | October | September | October |
| 'UF 4412' | 4.2 a | 4.0 | 4.3 | 3.8 b | 4.8 ab | 4.2 b | 4.9 | 4.5 a |
| 'Florida Red Ruffles' | 3.5 b | 4.3 | 4.0 | 5.0 a | 5.0 a | 4.7 a | 4.6 | 4.2 ab |
| 'Florida Sweetheart' | 3.5 b | 4.3 | 3.8 | 4.7 a | 4.5 b | 3.3 c | 4.6 | 3.8 b |
| 'UF 4424' | — | — | — | 5.0 a | 4.8 ab | 4.2 b | 4.9 | 4.7 a |
| LSD (α = 0.05) | 0.35 | NS | NS | 0.74 | 0.44 | 0.29 | NS | 0.58 |

[z]mean values with the same letter within columns are not significantly different at P < 0.05.
[y]this cultivar was not available for evaluation.
LSD: least significant differences; NS: Not significantly different at P < 0.05.

As shown in Table 3, with a superb number of large, wide lance leaves in bright red, plants of 'UF 4412' received very high plant performance ratings (4.2 to 4.9) in all evaluations in three growing seasons. Plant performance ratings of 'UF 4412' were significantly higher than those of 'Florida Red Ruffles' in all nine evaluations and significantly higher than those of 'Florida Sweetheart' in five out of nine evaluations.

As shown in Table 3, sunburn tolerance ratings of 'UF 4412' were between 3.8 and 4.9, which are similar to the sunburn tolerance ratings of 'Florida Red Ruffles' or 'Florida Sweetheart' in most of the evaluations.

The suitability of 'UF 4412' for pot plant production was evaluated by forcing tubers in 11.4-cm containers in spring 2008. Intact No. 1 tubers (>3.8 and <6.4 cm in diameter) were planted in a peat/vermiculite mix (VerGro Container Mix A, Verlite, Tampa, Fla.) on 17 Apr. 2008. The study was conducted in a greenhouse with 45% light exclusion. Average daily temperatures in the greenhouse ranged from a low of 16° C. night to 29° C. day during the experiment. Potted plants were arranged on metal benches in the greenhouse in a randomized complete block fashion with eight replications. Plant height, plant width, number of leaves, and foliar characteristics were recorded on 12 Jun. 2008, 8 weeks after planting. Quality of the potted *Caladium* plants was rated on a scale of 1 to 5, 1=very poor, few leaves, totally unacceptable as potted plants, and 5=very attractive, with many bright, colorful leaves, a full plant, a symmetrical shape, and an appropriate height.

Table 4 shows a comparison of number of days to sprout, plant height, plant width, leaf number, leaf length, leaf width, and quality rating of 'UF 4412' with 'Florida Sweetheart' and 'Florida Red Ruffles'.

TABLE 4

| Cultivars | Days to sprout[z] (no.) | Plant height (cm) | Plant width (cm) | Leaves (no.) | Leaf length (cm) | Leaf width (cm) | Quality rating |
|---|---|---|---|---|---|---|---|
| 'UF 4412' | 30.5 a[y] | 22.4 a | 50.5 a | 19.4 | 23.3 a | 15.9 a | 3.8 a |
| 'Fla. Red Ruffles' | 25.3 b | 18.3 b | 35.8 b | 19.1 | 17.9 b | 12.3 b | 2.7 b |
| 'Fla. Sweetheart' | 25.3 b | 16.0 b | 33.5 b | 19.0 | 19.2 b | 14.6 ab | 2.9 b |
| LSD (α = 0.05) | 2.38 | 2.91 | 4.93 | NS | 2.64 | 2.78 | 0.48 |

[z]Number of days from planting to the first unfurled leaf .
[y]Mean values within columns that share the same letters are not significantly different at P < 0.05.
NS: Not significantly different at P < 0.05.

As shown in Table 4, tubers of 'UF4412' sprouted ~30 days after planting, approximately 5 days later than tubers of 'Florida Red Ruffles' and 'Florida Sweetheart'. Plants of 'UF 4412' were 4 to 6 cm taller and 15 to 17 cm wider than plants of 'Florida Red Ruffles' and 'Florida Sweetheart' plants. Leaves of 'UF 4412' were 4 to 5 cm longer and 1 to 3 cm wider than leaves of 'Florida Red Ruffles' or 'Florida Sweetheart'. Pot-grown plants of 'UF4412' received significantly higher quality rating (3.8) than pot-grown plants of 'Florida Red Ruffles' and 'Florida Sweetheart' (2.7 to 2.9).

We claim:

1. A new and distinct *Caladium* plant named 'UF 4412' as illustrated and described herein.

* * * * *